(12) United States Patent
Okikawa et al.

(10) Patent No.: US 9,072,457 B2
(45) Date of Patent: Jul. 7, 2015

(54) OPTICAL IMAGE MEASUREMENT APPARATUS AND OPTICAL ATTENUATOR

(75) Inventors: Shigeru Okikawa, Tokyo (JP); Tomoyoshi Abe, Tokyo (JP)

(73) Assignee: KABUSHIKI KAISHA TOPCON, Tokyo (JP)

( * ) Notice: Subject to any disclaimer, the term of this patent is extended or adjusted under 35 U.S.C. 154(b) by 335 days.

(21) Appl. No.: 13/518,240

(22) PCT Filed: Nov. 16, 2010

(86) PCT No.: PCT/JP2010/006718
§ 371 (c)(1), (2), (4) Date: Jun. 21, 2012

(87) PCT Pub. No.: WO2011/077633
PCT Pub. Date: Jun. 30, 2011

(65) Prior Publication Data
US 2012/0257212 A1    Oct. 11, 2012

(30) Foreign Application Priority Data
Dec. 25, 2009   (JP) .................................. 2009-293978

(51) Int. Cl.
*G01B 9/02* (2006.01)
*A61B 3/10* (2006.01)
*G02B 26/04* (2006.01)

(52) U.S. Cl.
CPC ............... *A61B 3/102* (2013.01); *G02B 26/04* (2013.01)

(58) Field of Classification Search
CPC .............................................. G01B 9/02
USPC .......................................... 356/479; 600/178
See application file for complete search history.

(56) References Cited

U.S. PATENT DOCUMENTS

| 4,706,657 A * | 11/1987 | Miyagi .................. 600/178 |
| 6,377,349 B1 | 4/2002 | Fercher |
| 7,345,770 B2 | 3/2008 | Chan et al. |

(Continued)

FOREIGN PATENT DOCUMENTS

| JP | 02-285317 A | 11/1990 |
| JP | 04-035855 Y2 | 8/1992 |
| JP | 09-276232 A | 10/1997 |

(Continued)

OTHER PUBLICATIONS

International Search Report for PCT/JP2010/006718; Dec. 21, 2010.

*Primary Examiner* — Tarifur Chowdhury
*Assistant Examiner* — Jamil Ahmed
(74) *Attorney, Agent, or Firm* — Pearne & Gordon LLP (57) ABSTRACT

A cam face 303a of a cam 303 has a shape depending on the distribution of the light amount in the cross-section of reference light LR. When the cam 303 is rotated by a stepping motor 302, an abutment 312 moves following the displacement of the cam face 302a with the rotation of the cam 303. A light-blocking link 310 rotates about the axis of rotation 311 with the movement of the abutment 312. A shield 313 moves in a first direction with the rotation of the light-blocking link 310 to change the shielding region of the reference light LR. A light-blocking plate 400 can shield the reference light LR from a second direction different from a shielding direction (first direction) by an attenuator 300. The light-blocking plate 400 is moved by a drive mechanism 410 and changes the shielding region.

7 Claims, 7 Drawing Sheets

(56) References Cited

U.S. PATENT DOCUMENTS

2008/0117430 A1 5/2008 Terakawa et al.
2011/0080561 A1 4/2011 Hayashi et al.

FOREIGN PATENT DOCUMENTS

| JP | 11-325849 | A | | 11/1999 |
|---|---|---|---|---|
| JP | 2002-131659 | A | | 5/2002 |
| JP | 2002-139421 | A | | 5/2002 |
| JP | 2002139421 | A | * | 5/2002 |
| JP | 2006-153838 | A | | 6/2006 |
| JP | 2007-024677 | A | | 2/2007 |
| JP | 2008-073099 | A | | 4/2008 |
| JP | 2008-128710 | A | | 6/2008 |
| JP | 2008-145376 | A | | 6/2008 |
| JP | 2008-259544 | A | | 10/2008 |
| WO | 2009-153929 | A1 | | 6/2009 |

* cited by examiner

OPTICAL IMAGE MEASUREMENT APPARATUS AND OPTICAL ATTENUATOR

TECHNICAL FIELD

The present invention relates to an optical image measurement apparatus and an optical attenuator. The optical image measurement apparatus is an apparatus that forms images of a measured object by using optical coherence tomography (OCT). The optical attenuator is a device that changes attenuation amount of light.

BACKGROUND ART

In recent years, OCT that forms images of the surface morphology and internal morphology of an object by using a light beam from a laser light source or the like has attracted attention. Unlike an X-ray CT apparatus, optical coherence tomography is noninvasive to human bodies, and is therefore expected to be utilized in the medical field and biological field. For example, in the ophthalmology, devices that form images of a fundus and cornea or the like are in a practical stage.

Patent Document 1 discloses a device to which OCT is applied. This device has such a configuration that: a measuring arm scans an object by a rotary deflection mirror (a Galvano mirror); a reference arm is provided with a reference mirror; and an interferometer is mounted at the outlet to analyze, by a spectrometer, the intensity of an interference light of light fluxes from the measurement arm and the reference arm. Moreover, the reference arm is configured to gradually change the light flux phase of the reference light by discontinuous values.

The device of Patent Document 1 uses a technique of so-called "Fourier Domain OCT." That is to say, the device irradiates a low-coherence light beam to an object, superposes the reflected light and the reference light to generate an interference light, and acquires the spectral intensity distribution of the interference light to execute Fourier transform, thereby imaging the morphology in the depth direction (the z-direction) of the object. The technique of this type is also called Spectral Domain.

Furthermore, the device described in Patent Document 1 is provided with a Galvano mirror that scans with a light beam (a signal light), and is thereby configured to form an image of a desired measurement target region of the object. Because this device is configured to scan with the light beam only in one direction (the x-direction) orthogonal to the z-direction, an image formed by this device is a two-dimensional tomographic image in the depth direction (the z-direction) along the scanning direction (the x-direction) of the light beam.

Patent Document 2 discloses a technique of scanning with a signal light in the horizontal direction (x-direction) and the vertical direction (y-direction) to form a plurality of two-dimensional tomographic images in the horizontal direction, and acquiring and imaging three-dimensional tomographic information of a measured range based on the tomographic images. As the three-dimensional imaging, for example, a method of arranging and displaying a plurality of tomographic images in the vertical direction (referred to as stack data or the like), and a method of executing a rendering process on a plurality of tomographic images to form a three-dimensional image are considered.

Patent Documents 3 and 4 disclose other types of OCT devices. Patent Document 3 describes an OCT device that images the morphology of an object by sweeping the wavelength of light that is irradiated to an object, acquiring the spectral intensity distribution based on an interference light obtained by superposing the reflected lights of the light of the respective wavelengths on the reference light, and executing Fourier transform. Such an OCT device is called a Swept Source type or the like. The Swept Source type is a kind of the Fourier Domain type.

Further, Patent Document 4 describes an OCT device that irradiates a light having a predetermined beam diameter to an object and analyzes the components of an interference light obtained by superposing the reflected light and the reference light, thereby forming an image of the object in a cross-section orthogonal to the travelling direction of the light. Such an OCT device is called a full-field type, en-face type or the like.

Patent Document 5 discloses an example of applying OCT to the ophthalmologic field. In addition, before OCT was applied, a retinal camera, a slit lamp, etc. were used as devices for observing an eye (e.g., see Patent Documents 6 and 7). The retinal camera is a device that photographs the fundus oculi by projecting illumination light onto the eye and receiving the reflected light from the fundus oculi. The slit lamp is a device that obtains an image of the cross-section of the cornea by cutting off the light section of the cornea using slit light.

The device with OCT is superior relative to the retinal camera, etc. in that high-definition images can be obtained, further in that tomographic images and three-dimensional images can be obtained, etc.

Optical image measurement apparatuses that apply OCT include those provided with an optical attenuator (sometimes simply referred to as "attenuator") for adjusting light amount (intensity). For example, in Patent Document 8, an attenuator is described that attenuates respective wavelength bands at different attenuation factors to make the light amount uniform. This attenuator adjusts the attenuation factors using a rotatable neutral density filter.

In addition, it is common for attenuators to shield light with a light-blocking material (e.g., see Patent Document 9). Moreover, in Patent Document 9, a configuration is disclosed that uses two attenuators disposed facing across a parallel beam. The purpose of this configuration is to eliminate any limitations on the direction of travel of light beams and to uniformly shield light beams.

PRIOR ART DOCUMENTS

Patent Documents

[Patent Document 1]
    Japanese Unexamined Patent Application Publication No. Hei 11-325849
[Patent Document 2]
    Japanese Unexamined Patent Application Publication No. 2002-139421
[Patent Document 3]
    Japanese Unexamined Patent Application Publication No. 2007-24677
[Patent Document 4]
    Japanese Unexamined Patent Application Publication No. 2006-153838
[Patent Document 5]
    Japanese Unexamined Patent Application Publication No. 2008-73099
[Patent Document 6]
    Japanese Unexamined Patent Application Publication No. Hei 9-276232

[Patent Document 7]
Japanese Unexamined Patent Application Publication No. 2008-259544
[Patent Document 8]
Japanese Unexamined Patent Application Publication No. 2008-145376
[Patent Document 9]
Japanese Unexamined Patent Application Publication No. 2002-131659

SUMMARY OF THE INVENTION

Problem that the Invention is to Solve

In OCT, it is necessary to precisely adjust the light amount in order to suitably detect interference light. However, with conventional attenuators, it has been difficult to meet this requirement. The reason for this is that the output light amount of a light source varies with time degradation and the environment, so it may not be possible to use the same light amount all the time. Furthermore, the light amount of interference light may be varied through displacement of a collimator that makes a light beam, which is the subject of adjustment of light amount, to be a parallel pencil.

Moreover, with conventional attenuators, the operational accuracy required to perform suitable OCT measurement often cannot be achieved. For example, if the amount of light used is large, the majority of this light is shielded to make a proper light amount; however, precise control is required in order to adjust the light amount under this condition with high accuracy. In other words, because the light passing through the attenuator makes up a small portion of the original light, to change the amount of this passing light, e.g., by several percent, the shielding material must be moved by an extremely minute distance.

Moreover, while the amount of movement of a shield plate when changing the light amount by a predefined amount depends on the amount of original light (the amount of movement decreases with increases in the light amount), precise control has been required in order to realize control of the amount of movement according to the amount of original light with conventional attenuators.

In addition, although it is possible to attempt to improve the operational accuracy using a high-resolution stepping motor, there are demerits such as making the mechanism large and complicated, and further, increased cost.

This invention resolves the above-mentioned problem, with the purpose of providing an optical attenuator capable of precisely adjusting the light amount with a simple configuration, and providing an optical image measurement apparatus capable of suitably detecting interference light through the use of this optical attenuator.

Means for Solving the Problem

In order to achieve the aforementioned objects, an invention according to Claim 1 is an optical image measurement apparatus comprising: an optical system that splits low-coherence light into signal light and reference light, generates and detects interference light by superposing the signal light that has passed through a signal optical path toward a measured object and the reference light that has passed through a reference optical path; and an image-forming part that forms an image of the measured object based on the detection result of the interference light; the optical image measurement apparatus comprising: an optical attenuator that is respectively provided in at least one subject optical path of an optical path of the low-coherence light, the signal optical path, the reference optical path, and an optical path of the interference light, and capable of shielding subject light traveling in the subject optical path; the optical attenuator comprising: a stepping motor, a cam that has a cam surface shaped depending on the distribution of the light amount in the cross-section of the subject light, and that is rotated by the stepping motor; a shielding mechanism including an abutment that abuts the cam face, an axis of rotation provided at a predefined distance away from the abutment, and a first shield that is provided at a predefined distance away from the axis of rotation and capable of shielding the subject light from a first direction; and a second shield that is capable of shielding the subject light from a second direction different from the first direction; wherein, in response to the rotation of the cam by the stepping motor: the abutment moves following the displacement of the cam face with the rotation of the cam; the shielding mechanism rotates about the axis of rotation with the movement of the abutment; the first shield moves in the first direction with the rotation of the shielding mechanism to change the shielding region of the subject light; the optical system detects the interference light based on the subject light, part of which is shielded by the first shield and the second shield; and the image-forming part forms an image of the measured object based on the detection result of this interference light.

Further, an invention according to Claim 2 is the optical image measurement apparatus according to Claim 1, wherein the cam face is formed so that based on Gaussian distribution as the distribution of the light amount, and with increase in the shielding region of the subject light by the first shield, the amount of movement of the first shield in the first direction corresponding to the amount of unit rotation of the stepping motor is small.

Further, an invention according to Claim 3 is the optical image measurement apparatus according to Claim 1, wherein the optical attenuator comprises a drive mechanism that moves the second shield to change the shielding region of the subject light.

Further, an invention according to Claim 4 is the optical image measurement apparatus according to Claim 3, wherein: a side of a tip of the first shield is formed in a substantially linear fashion in a radial direction relative to the rotational direction of the shielding mechanism about the axis of rotation; a side of a tip of the second shield is formed in a substantially linear fashion, which is oblique relative to the radial direction with the side of the first shield disposed at a position to shield the subject light; and the drive mechanism moves the second shield in a direction substantially perpendicular to the radial direction to change the shielding region of the subject light.

Further, an invention according to Claim 5 is the optical image measurement apparatus according to Claim 1, wherein the second shield shields only the central region of the cross-section of the subject light.

Further, an invention according to Claim 6 is the optical image measurement apparatus according to Claim 1, wherein the first shield and/or the second shield are disposed leaning to the cross-section of the subject light.

Further, an invention according to Claim 7 is an optical attenuator that is capable of shielding a light beam, the optical attenuator comprising: a stepping motor; a cam that has a cam surface shaped depending on the distribution of the light amount in the cross-section of the subject light, and that is rotated by the stepping motor; and a shielding mechanism including an abutment that abuts the cam face, an axis of rotation provided at a predefined distance away from the abutment, and a first shield that is provided at a predefined distance away from the axis of rotation and can shield the light beam from a first direction; wherein, in response to the rotation of the cam by the stepping motor: the abutment moves following the displacement of the cam face with the rotation of the cam; the shielding mechanism rotates about the axis of rotation with the movement of the abutment; and the first shield moves in the first direction with the rotation of the shielding mechanism to change the shielding region of the light beam.

Effect of the Invention

The optical image measurement apparatus related to the present invention comprises an optical attenuator that shields subject light from two different directions, allowing the light amount to be precisely adjusted compared to when shielding from only a single direction. Furthermore, by devising the shape of the cam face, it is possible to precisely adjust the light amount regardless of the shielding region of the subject light. Thereby, it is possible to suitably detect interference light.

The optical attenuator related to the present invention is configured to shield subject light from two different directions, so it is able to precisely adjust the light amount compared to when shielding from only a single direction. Furthermore, by devising the shape of the cam face, it is possible, without using a high-resolution stepping motor, to precisely adjust the light amount regardless of the shielding region of the subject light. Therefore, it is possible to precisely adjust the light amount with a simple configuration.

MODE FOR CARRYING OUT THE INVENTION

An example of an embodiment of an optical image measurement apparatus according to the present invention will be described in detail with reference to the drawings.

The optical image measurement apparatus according to the present invention forms tomographic images of a measured object using optical coherence tomography. This optical image measurement apparatus uses OCT of any type. It should be noted that an image obtained by OCT is sometimes referred to as an OCT image. Furthermore, a measuring action for forming an OCT image is sometimes referred to as an OCT measurement.

In the following embodiments, an apparatus that performs measurement of a fundus by applying OCT of a Fourier-Domain-type, similar to a device disclosed in, for example, Patent Document 5, is described in detail.

[Configuration]

Figure 1:
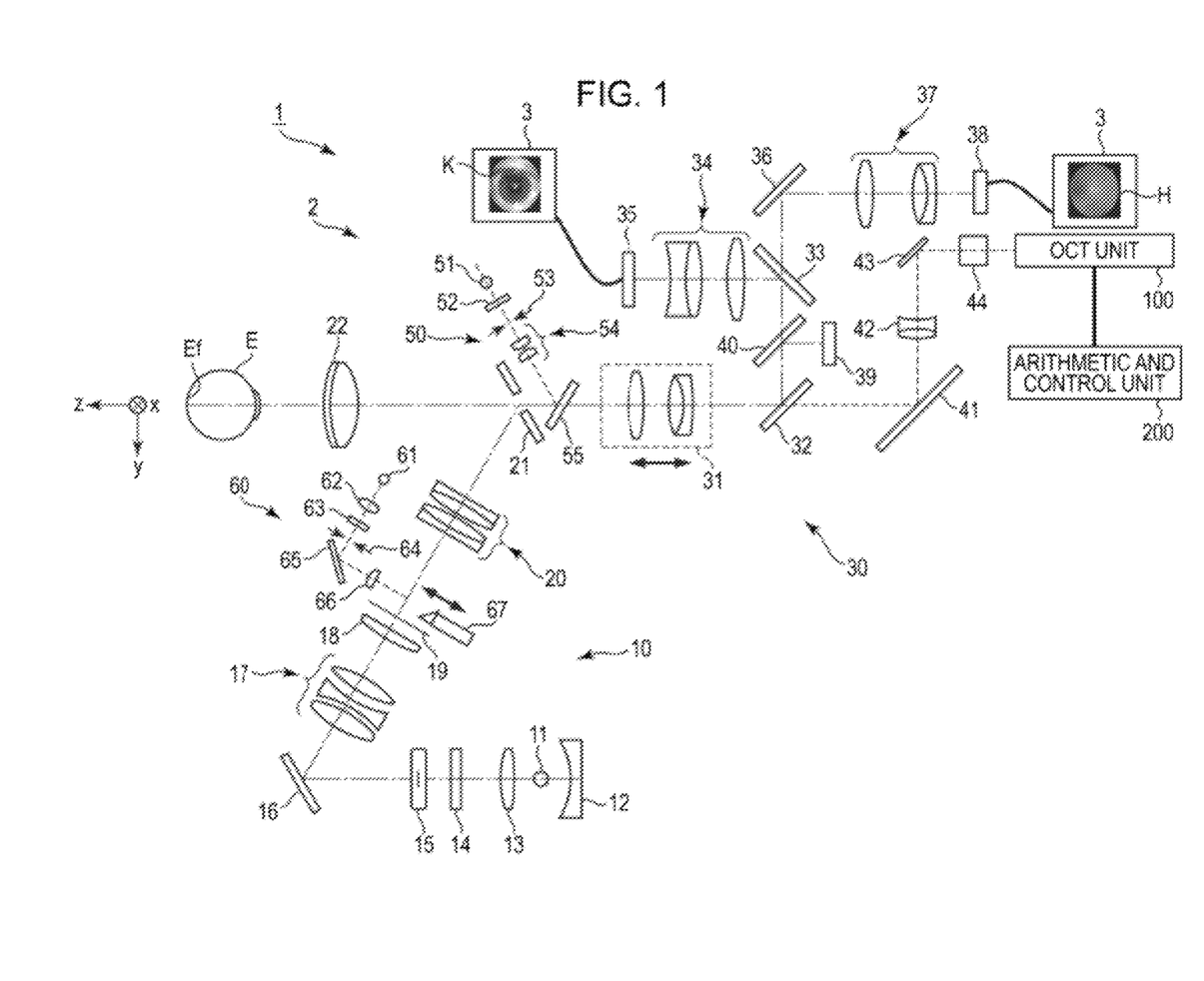
FIG. 1 is a schematic view showing an example of a configuration of an embodiment of an optical image measurement apparatus (fundus observation apparatus) according to the present invention.
Figure 2:
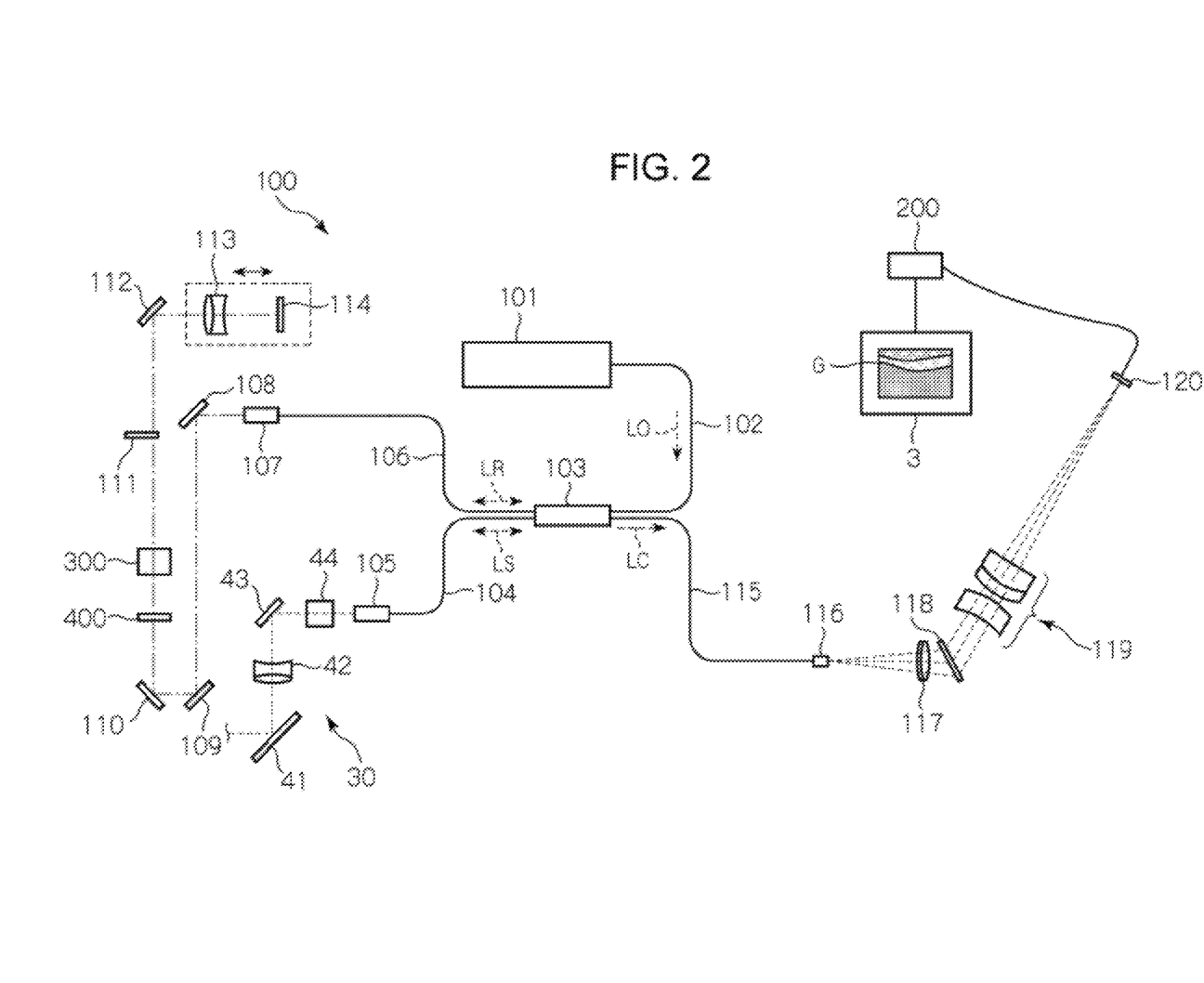
FIG. 2 is a schematic view showing an example of a configuration of an embodiment of an optical image measurement apparatus (fundus observation apparatus) according to the present invention.

A fundus observation apparatus 1, as shown in FIG. 1 and FIG. 2, includes a retinal camera unit 2, an OCT unit 100, and an arithmetic and control unit 200. The retinal camera unit 2 has almost the same optical system as a conventional retinal camera. The OCT unit 100 is provided with an optical system for obtaining an OCT image of a fundus. The arithmetic and control unit 200 is provided with a computer that executes various arithmetic processes, control processes, and so on.

[Retinal Camera Unit]

The retinal camera unit shown in FIG. 1 is provided with an optical system for forming a 2-dimensional image (fundus image) representing the surface morphology of the fundus Ef of an eye E. Fundus images include observation images, photographed images, etc. The observation image is, for example, a monochrome moving image formed at a prescribed frame rate using near-infrared light. The photographed image is, for example, a color image captured by flashing visible light. It should be noted that the retinal camera unit 2 may also be configured so as to be capable of capturing other types of images such as a fluorescein angiography image, an indocyanine green fluorescent image, and an autofluorescent image.

The retinal camera unit 2 is provided with a chin rest and a forehead placement for retaining the face of the subject, similar to a conventional retinal camera. Moreover, like a conventional retinal camera, the retinal camera unit 2 is provided with an illumination optical system 10 and an imaging optical system 30. The illumination optical system 10 irradiates an illumination light to the fundus Ef. The imaging optical system 30 guides a fundus reflected light of the illumination light to imaging devices (CCD image sensors 35, 38). Moreover, the imaging optical system 30 guides a signal light LS coming from the OCT unit 100 to the fundus Ef, and guides the signal light propagated through the fundus Ef to the OCT unit 100.

An observation light source 11 of the illumination optical system 10 comprises, for example, a halogen lamp. Light (observation illumination light) output from the observation light source 11 is reflected by a reflection mirror 12 with a curved reflection surface, and becomes near infrared after passing through a visible cut filter 14 via a condenser lens 13. Furthermore, the observation illumination light is once converged near an imaging light source 15, reflected by a mirror 16, and passes through relay lenses 17, 18, diaphragm 19, and relay lens 20. Then, the observation illumination light is reflected on the peripheral part (the surrounding region of an aperture part) of an aperture mirror 21 and illuminates the fundus Ef via an object lens 22.

The fundus reflection light of the observation illumination light is refracted by the object lens 22, passes through the aperture part formed in the center region of the aperture mirror 21, passes through a dichroic mirror 55 and, travels through a focusing lens 31, and is reflected by a dichroic mirror 32. Furthermore, the fundus reflection light passes through a half-mirror 40 and forms an image on the light receiving surface of the CCD image sensor 35 by a condenser lens 34 after being reflected by a dichroic mirror 33. The CCD image sensor 35 detects, for example, the fundus reflection light at a prescribed frame rate. An image (observation image) K based on the fundus reflection light detected by the CCD image sensor 35 is displayed on a display device 3.

The imaging light source 15 consists of, for example, a xenon lamp. The light (imaging illumination light) output from the imaging light source 15 is irradiated to the fundus Ef via a route that is similar to the observation illumination light. The fundus reflection light of the imaging illumination light is guided to the dichroic mirror 33 via the same route as that of the observation illumination light, passes through the dichroic mirror 33, and forms an image on the light receiving surface of the CCD image sensor 38 by a condenser lens 37 after being reflected by a mirror 36. An image (photographed image) H based on the fundus reflection light detected by the CCD image sensor 38 is displayed on the display device 3. It should be noted that the display device 3 for displaying an observation image K and the display device 3 for displaying a photographed image H may be the same or different.

An LCD (Liquid Crystal Display) 39 displays a fixation target or a visual target for measuring eyesight. The fixation target is a visual target for fixing the eye E, and is used when photographing a fundus or performing an OCT measurement.

Part of the light output from the LCD 39 is reflected by a half-mirror 40, reflected by the dichroic mirror 32, passes through the aperture part of the aperture mirror 21 via the focusing lens 31 as well as a dichroic mirror 55, is refracted by the object lens 22 and projected to the fundus Ef.

By changing a display position of the fixation target on the screen of the LCD 39, it is possible to change a fixation position of the eye E. As the fixation position of the eye E, there are a position for acquiring an image centered on the macula of the fundus Ef, a position for acquiring an image centered on the optic papilla, a position for acquiring an image centered on the fundus center between the macula and the optic papilla, and so on, for example, as in conventional retinal cameras.

Furthermore, as with conventional retinal cameras, the retinal camera unit 2 is provided with an alignment optical system 50 and a focus optical system 60. The alignment optical system 50 generates a target (alignment target) for matching the position (alignment) of the device optical system with respect to the eye E. The focus optical system 60 generates a target (split target) for matching the focus with respect to the eye Ef.

Light (alignment light) output from the LED (Light Emitting Diode) 51 of the alignment optical system 50 is reflected by the dichroic mirror 55 via diaphragms 52, 53 and a relay lens 54, passes through the aperture part of the aperture mirror 21, and is projected onto the cornea of the eye E by the object lens 22.

Part of cornea reflection light of the alignment light is transmitted through the dichroic mirror 55 via the object lens 22 and the aperture part, passes through the focusing lens 31, is reflected by the dichroic mirror 32, transmitted through the half-mirror 40, reflected by the dichroic mirror 33, and projected onto the light receiving surface of the CCD image sensor 35 by the condenser lens 34. An image (alignment target) captured by the CCD image sensor 35 is displayed on the display device 3 along with the observation image K. A user conducts alignment by an operation that is the same as conventional retinal cameras. It should be noted that alignment may be performed, by an arithmetic and control unit 200, as a result of analyzing the position of the alignment target and moving the optical system.

In order to conduct focus adjustment, the reflection surface of a reflection rod 67 is provided in a slanted position on the optical path of the illumination optical system 10. Light (focus light) output from an LED 61 of the focus optical system 60 passes through a relay lens 62, is split into two light fluxes by a split target plate 63, passes through a two-hole diaphragm 64, is reflected by a mirror 65, and is reflected after an image is formed once on the reflection surface of the reflection rod 67 by a condenser lens 66. Furthermore, the focus light is reflected at the aperture mirror 21 via the relay lens 20 and an image is formed on the fundus Ef by the object lens 22.

The fundus reflection light of the focus light passes through the same route as the cornea reflection light of the alignment light and is detected by the CCD image sensor 35. A light (split target) captured by the CCD image sensor 35 is displayed on the display device 3 along with an observation image K. The arithmetic and control unit 200, as in the past, analyzes the position of the split target, and moves the focusing lens 31 and the focus optical system 60 for focusing. It should be noted that focusing may be performed manually while visually recognizing the split target.

An optical path including a mirror 41, collimator lens 42, and Galvano mirrors 43, 44 is provided behind the dichroic mirror 32. The optical path is connected to the OCT unit 100.

The Galvano mirror 44 performs scanning with a signal light LS from the OCT unit 100 in the x-direction. The Galvano mirror 43 performs scanning with a signal light LS in the y-direction. Scanning may be performed with the signal light LS in an arbitrary direction in the xy-plane due to the two Galvano mirrors 43 and 44.

[OCT Unit]

The OCT unit 100 is provided with an optical system for obtaining a tomographic image of the fundus Ef (see FIG. 2). The optical system has a similar configuration to a conventional Fourier-Domain-type OCT device. That is to say, the optical system is configured to split low-coherence light into signal light and reference light, generate interference light by interfering the signal light that has passed through the fundus Ef and the reference light that has passed through a reference optical path, and detect the spectral components of the interference light. This detection result (detection signal) is transmitted to the arithmetic and control unit 200.

A light source unit 101 outputs a broadband low-coherence light L0. The low-coherence light L0, for example, includes near-infrared wavelength bands (about 800-900 nm) and has a coherence length of about tens of micrometer. Moreover, it is possible to use, as the low-coherence light L0, near-infrared light having wavelength bands that are impossible to be detected by human eyes, for example, infrared light having the center wavelength of about 1050-1060 nm.

The light source unit 101 is configured to include light output device, such as an SLD (super luminescent diode), LED, SOA (Semiconductor Optical Amplifier) and the like.

The low-coherence light L0 output from the light source unit 101 is guided to a fiber coupler 103 by an optical fiber 102 and split into signal light LS and reference light LR. It should be noted that the fiber coupler 103 acts both as a means to split light (splitter) as well as a means to synthesize light (coupler), but herein the same is conventionally referred to as a "fiber coupler."

The signal light LS is guided by the optical fiber 104 and becomes a parallel light flux by a collimator lens unit 105. Furthermore, the signal light LS is reflected by Galvano mirrors 44 and 43, converged by the collimator lens 42, reflected by the mirror 41, transmitted through a dichroic mirror 32, and irradiated to the fundus Ef after passing through a route that is the same as the light from the LCD 39. The signal light LS is scattered and reflected at the fundus Ef. The scattered light and the reflection light are sometimes all together referred to as the fundus reflection light of the signal light LS. The fundus reflection light of the signal light LS progresses along the same route in the reverse direction and is guided to the fiber coupler 103.

The reference light LR is guided by an optical fiber 106 and becomes a parallel light flux by a collimator lens unit 107. Furthermore, the reference light LR is reflected by mirrors 108, 109, 110, passed through a light-blocking plate 400 and an attenuator 300, dimmed by an ND (Neutral Density) filter 111, and reflected by a mirror 112, with the image formed on a reflection surface of a reference mirror 114 by a collimator lens 113. The reference light LR reflected by the reference mirror 114 progresses along the same route in the reverse direction and is guided to the fiber coupler 103. It should be noted that an optical element for dispersion compensation (pair prism, etc.) and/or an optical element for polarization correction (wave plate, etc.) may also be provided for the optical path (reference optical path) of the reference light LR.

The fiber coupler 103 superposes the fundus reflection light of the signal light LS and the reference light LR reflected by the reference mirror 114. Interference light LC thus generated is guided by an optical fiber 115 and output from an exit end 116. Furthermore, the interference light LC is converted to a parallel light flux by a collimator lens 117, spectrally divided (spectrally decomposed) by a diffraction grating 118, converged by the convergence lens 119, and projected onto the light receiving surface of a CCD image sensor 120. The diffraction grating 118 shown in FIG. 2 is of the transmission type, but the reflection type can also be used.

The CCD image sensor 120 is for example a line sensor, and detects the respective spectral components of the spectrally decomposed interference light LC and converts the components into electric charges. The CCD image sensor 120 accumulates these electric charges and generates a detection signal. Furthermore, the CCD image sensor 120 transmits the detection signal to the arithmetic and control unit 200.

Although a Michelson-type interferometer is employed in this embodiment, it is possible to employ any type of interferometer such as a Mach-Zehnder-type as necessary. Instead of a CCD image sensor, other types of image sensors, such as a CMOS (Complementary Metal Oxide Semiconductor) image sensor, can be used.

[Regarding the Attenuator]

Now, the attenuator 300 and the light-blocking plate 400 will be described. As described previously, reference light LR passing through the attenuator 300 and the light-blocking plate 400 is a parallel pencil. The combination of the attenuator 300 and the light-blocking plate 400 is an example of the "optical attenuator" of the present invention. In this embodiment, the light to be shielded by the optical attenuator (subject light) is reference light LR.

Specific examples of the attenuator 300 and the light-blocking plate 400 are described in reference to FIGS. 3-8. In addition, although the light-blocking plate 400 in this embodiment is disposed on the fiber coupler 103 side of the attenuator 300 in the reference optical path, it may be disposed on the reference mirror 114 side.

Figure 3:
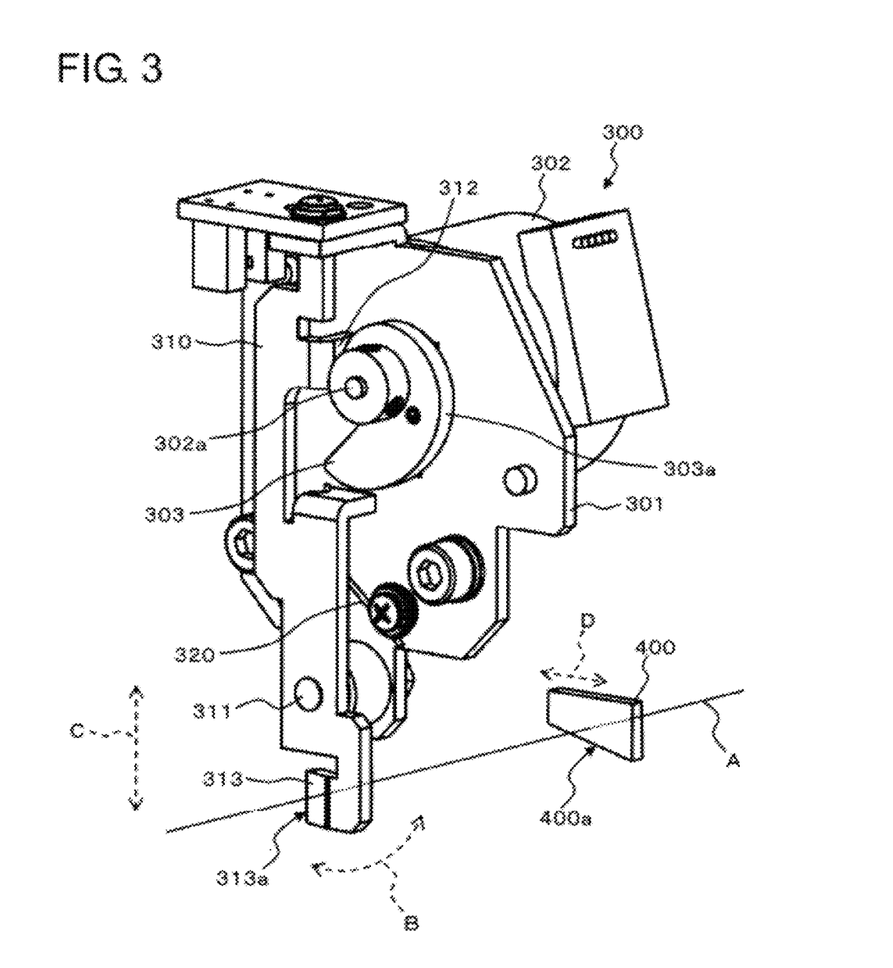
FIG. 3 is a perspective view showing an example of a configuration of an optical attenuator provided in an embodiment of an optical image measurement apparatus (fundus observation apparatus) according to the present invention.

A retaining plate 301 of the attenuator 300 is attached to a housing (not shown) of the OCT unit 100, for example. The retaining plate 301 retains various members described later. A stepping motor 302 is mounted on one side of the retaining plate 301. The stepping motor 302 receives a pulse signal (drive pulse) from the arithmetic and control unit 200, and rotates the axis of rotation 302a by the amount of rotation according to the pulse number thereof. The axis of rotation 302a penetrates the retaining plate 301 and protrudes to the other side.

A cam 303 is mounted on the axis of rotation 302a. The cam 303 integrally rotates with the axis of rotation 302a. The cam 303 has a cam face 303a with a characteristic shape as follows. The cam face 303a is a peripheral surface of the cam 303.

Meanwhile, the cross-section of the reference light LR (orthogonal cross-section relative to the direction of travel) has a predefined light amount distribution. This light amount distribution is approximated by Gaussian distribution. Subsequently, assuming that the light amount distribution for the reference light LR is a Gaussian distribution, a cam curve is obtained. This cam curve is a curve with a shape that prescribes the movement to be generated for the cam 303.

Furthermore, this cam curve is set such that with increases in the shielding region of the reference light LR by the attenuator 300, the amount of movement of a shield 313 (described later) corresponding to the amount of unit rotation of the stepping motor 302 becomes small. Here, the amount of unit rotation of the stepping motor 302 means the minimum angle of rotation by the stepping motor 302 (e.g., angle of rotation corresponding to 1 pulse). The amount of unit rotation is referred to as the step angle, etc. Moreover, the amount of movement of the shield 313 means the movement distance of the shield 313 when the stepping motor 302 drives by the amount of unit rotation. This amount of movement represents the positioning accuracy of the attenuator 300, which is referred to as resolution, etc. In other words, the cam curve is set such that the more widely shielded the reference light LR is, the higher the resolution.

The cam face 303a is formed, for example, by grinding the rim of the original form of the cam 303 along the cam curve set in this manner. As shown in FIG. 3, the cam 303 has a shape just like a comma-shaped gem. The axis of rotation 302a is disposed eccentrically on one side of the cam 303.

On the same side as the cam 303 in the retaining plate 301, a light-blocking link 310 is attached via the axis of rotation 311. The light-blocking link 310 is a member that changes the shielding region of the reference light LR in response to the operation of the cam 303. The light-blocking link 310 is one example of the "shielding mechanism" of the present invention. The axis of rotation 311 is arranged at a position near (the optical axis A of) the reference optical path for the light-blocking link 310. The light-blocking link 310 rotates (swings) about the axis of rotation 311. The rotational direction of the light-blocking link 310 is indicated by the symbol B (see FIG. 3, etc.).

In the light-blocking link 310, an abutment 312 that abuts the cam face 303a is formed. The abutment 312 is established at a position opposite the reference optical path across the axis of rotation 311. The abutment 312 has a face that contacts the cam face 303a. The light-blocking link 310 is biased by the elastic force of a spring 320 in a direction that presses the abutment 312 against the cam face 303a. Thereby, when the cam 303 rotates, the abutment 312 follows the displacement of the cam face 303a. In other words, with the rotation of the cam 303, the distance of the portion facing the abutment 312 in the cam face 303a from the axis of rotation 302a is displaced; however, with the action of the spring 320, the abutment 312 displaces together with the cam face 303a while maintaining the abutting status relative to the cam face 303a. With this displacement of the abutment 312, the light-blocking link 310 swings about the axis of rotation 311.

At the end opposite the abutment 312 in the light-blocking link 310, a shield 313 is established. The shield 313 is an example of the "first shield" of the present invention. The shield 313 is inserted and removed relative to the reference optical path by the swing of the light-blocking link 310. The shield 313 is a plate-like member that extends in the light-blocking link 310 in the insertion and removal direction relative to the reference light. A side 313a of the tip in the shield 313 on the side inserted into the reference optical path is formed in a substantially linear fashion in the radial direction C relative to the rotational direction B of the light-blocking link 310. Thereby, the light-blocking link 310 is inserted into the reference optical path from the right direction in FIG. 3, and its shielding region becomes one side region that is obtained by cutting a disk with a straight line (see the shielding region UR with oblique lines in FIGS. 6A and 6B).

The face onto which the reference light LR is irradiated in the shield 313 (irradiated face) leans to the above-mentioned cross-section of the reference light LR. That is, the shield 313 is arranged such that the normal direction of the irradiated face leans to the optical axis A of the reference optical path. Thereby, it is possible to avoid a situation in which reflected light of the reference light LR by the irradiated face gets mixed with the interference light LC. Similarly, for the light-blocking plate 400, its irradiated face is disposed leaning to the optical axis A.

Figure 4:
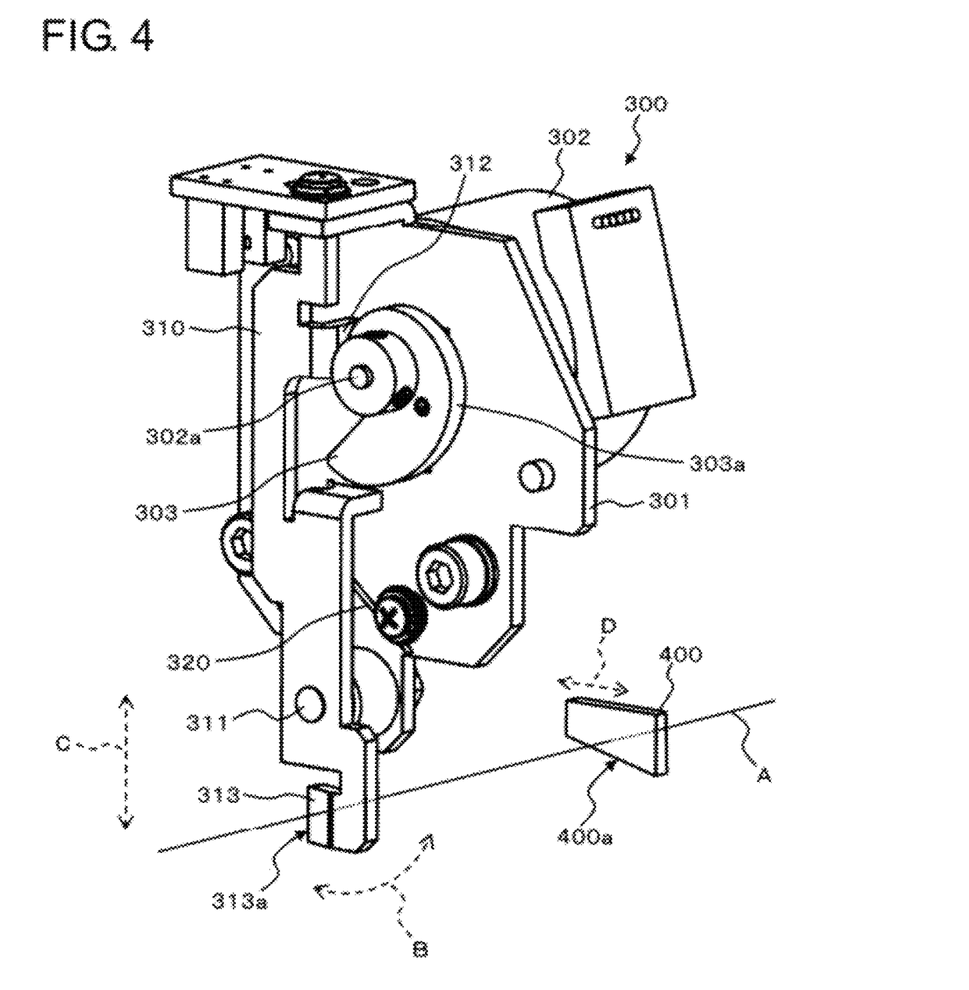
FIG. 4 is a side view showing an example of an action of an optical attenuator provided in an embodiment of an optical image measurement apparatus (fundus observation apparatus) according to the present invention.
Figure 5:
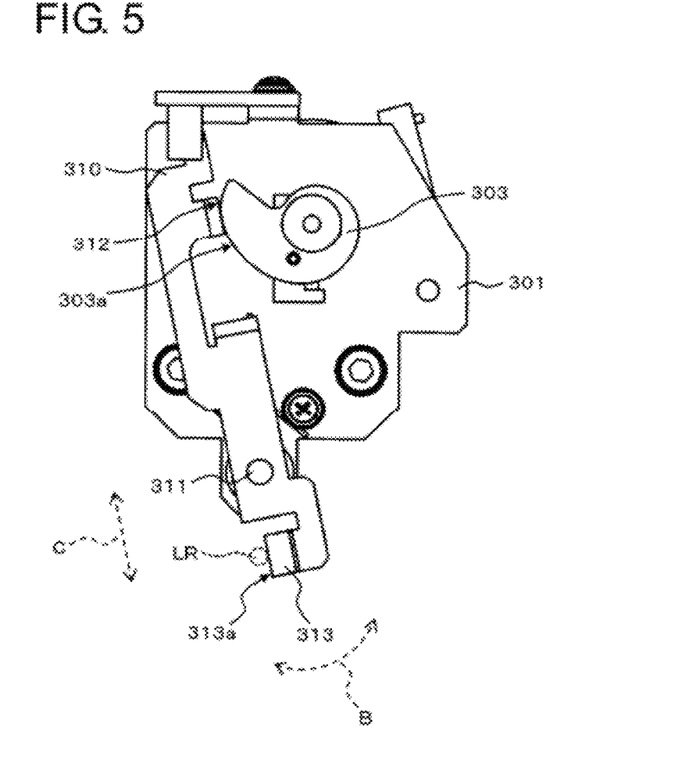
FIG. 5 is a side view showing an example of an action of an optical attenuator provided in an embodiment of an optical image measurement apparatus (fundus observation apparatus) according to the present invention.

FIG. 4 represents the condition in which the shield 313 completely shields the reference optical path, that is, the condition in which the reference light LR does not pass through at all. Moreover, FIG. 5 represents the condition in which the shield 313 completely opens the reference optical path, that is, the condition in which all the reference light LR passes through (in more detail, in which if the light is blocked by the light-blocking plate 400, all the passing light thereof passes through). The light-blocking link 310 shields/opens the reference optical path by performing such a rotating (swinging) operation in response to the rotation of the cam 303. In addition, as shown in the figures, with the rotating operation of the light-blocking link 310, the direction (i.e., radial direction C) of the side 313a of the tip of the shield 313 changes.

Figure 6A:
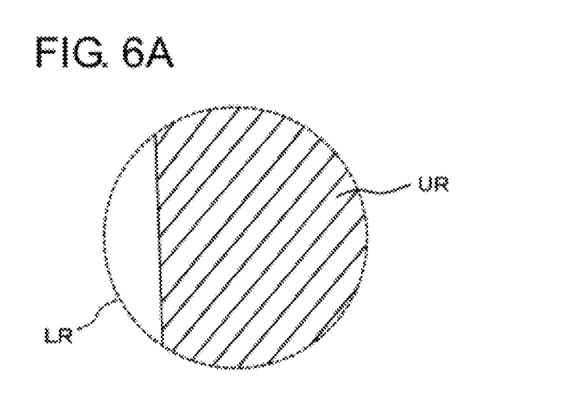
FIG. 6A is a schematic view for explaining a light shielding mode by an optical attenuator provided in an embodiment of an optical image measurement apparatus (fundus observation apparatus) according to the present invention.
Figure 6B:
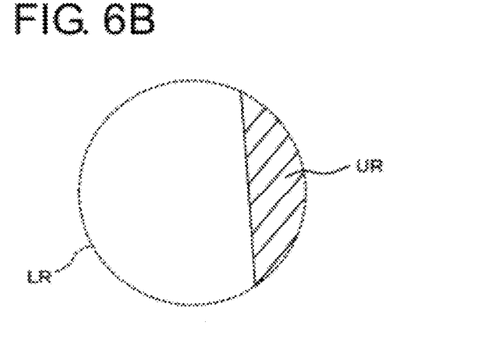
FIG. 6B is a schematic view for explaining a light shielding mode by an optical attenuator provided in an embodiment of an optical image measurement apparatus (fundus observation apparatus) according to the present invention.

FIGS. 6A and 6B represent the changed conditions of the shielding region UR of the reference light LR by the attenuator 300. FIG. 6A represents the condition in which much of the reference light LR (shielding region UR) is shielded by the attenuator 300 and the light corresponding to the remaining small portion thereof passes through. On the other hand, FIG. 6B represents the condition in which a small portion of the reference light LR (shielding region UR) is shielded by the attenuator 300 and the light corresponding to the remaining large portion thereof passes through.

In addition, because the cam face 303a has a shape as described above, the resolution of the shielding operation is high in the condition shown in FIG. 6A and low in the condition shown in FIG. 6B. Consequently, it is possible to adjust the light amount with accuracy according to the size of the shielding region UR of the reference light LR (i.e., the light amount of reference light LR used for OCT measurement).

Next, the light-blocking plate 400 is described. The light-blocking plate 400 can be inserted and removed relative to (the optical axis A of) the reference optical path. The light-blocking plate 400 is moved by a drive mechanism 410 described later, and shields the reference light LR from a direction different from that of the attenuator 300. The moving direction of the light-blocking plate 400 is indicated by the symbol D (see FIG. 3, etc.). The light-blocking plate 400 is an example of the "second shield" of the present invention. In addition, the shielding direction (first direction) by the attenuator 300 is the rotational direction B of the light-blocking link 310, and the shielding direction (second direction) by the light-blocking plate 400 is the direction perpendicular to the moving direction D of the light-blocking plate 400.

Figure 7A:
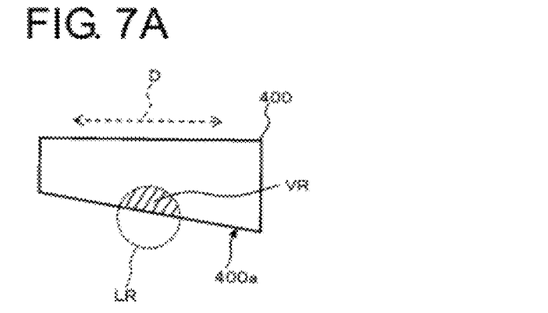
FIG. 7A is a schematic view for explaining a light shielding mode by an optical attenuator provided in an embodiment of an optical image measurement apparatus (fundus observation apparatus) according to the present invention.

As shown in FIG. 7A, etc., the light-blocking plate 400 is a plate-like member in which the face upon which the reference light LR is irradiated is formed into a trapezoidal shape. With the light-blocking plate 400, a region on the side of a tip 400a corresponding to an oblique line of this trapezoidal shape shields the reference light LR. The moving direction D of the light-blocking plate 400 is the direction in which a side facing this oblique line (bottom line) extends. Thus, when the light-blocking plate 400 is moved in the direction D, the oblique line is displaced just like moving the reference optical path up and down.

Furthermore, in the status in which the side 313a of the tip of the shield 313 is disposed at a position to shield the reference light LR, the side of the tip (tip 400a) of the light-blocking plate 400 is formed in a substantially linear fashion which is oblique relative to the radial direction C. In other words, as described previously, while the radial direction C changes its orientation with the rotation of the light-blocking link 310, for the case in which the shield 313 shields at least a portion of the reference light LR, the tip 400a (formed in a substantially linear fashion) of the light-blocking plate 400 will be oblique relative to the radial direction C at this time. Thereby, the attenuator 300 and the light-blocking plate 400 can shield the reference light LR from directions different from each other. Moreover, the drive mechanism 410 will move the light-blocking plate 400 in the direction D substantially perpendicular to the radial direction C at this time to change the shielding region of the reference light LR.

Figure 7B:
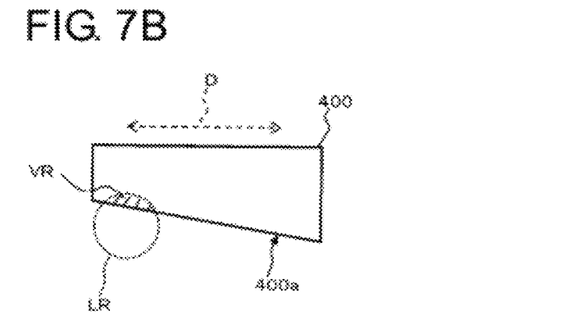
FIG. 7B is a schematic view for explaining a light shielding mode by an optical attenuator provided in an embodiment of an optical image measurement apparatus (fundus observation apparatus) according to the present invention.

FIGS. 7A and 7B represent the changed conditions of the shielding region VR of the reference light LR by the light-blocking plate 400. FIG. 7A represents the condition in which a little less than half of the reference light LR (shielding region VR) is shielded by the light-blocking plate 400 and the light corresponding to a little more than another half thereof passes through. On the other hand, FIG. 7B represents the condition in which a small portion of the reference light LR (shielding region VR) is shielded by the light-blocking plate 400 and the light corresponding to the remaining large portion thereof passes through.

Figure 8:
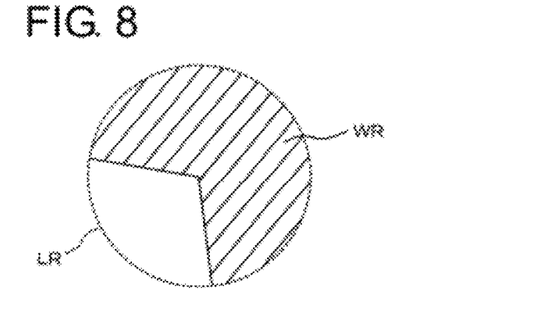
FIG. 8 is a schematic view for explaining a light shielding mode by an optical attenuator provided in an embodiment of an optical image measurement apparatus (fundus observation apparatus) according to the present invention.

An example of the shielding condition of the reference light LR when the attenuator 300 and the light-blocking plate 400 are used in combination is shown in FIG. 8. The shielding region WR shown in FIG. 8 is obtained by shielding about half of the reference light LR from the right of the page with the attenuator 300 and further shielding about half from above on the page with the light-blocking plate 400.

[Arithmetic and Control Unit]

A configuration of the arithmetic and control unit 200 will be described. The arithmetic and control unit 200 analyzes the detection signals inputted from the CCD image sensor 120, and forms an OCT image of the fundus Ef. An arithmetic process for this is the same as that of a conventional Fourier-Domain-type OCT device.

Further, the arithmetic and control unit 200 controls each part of the retinal camera unit 2, the display device 3 and the OCT unit 100. For example, the arithmetic and control unit 200 causes an OCT image such as a tomographic image G (see FIG. 2) of the fundus Ef to be displayed on the display device 3.

As control of the retinal camera unit 2, the arithmetic and control unit 200 executes: control of action of the observation light source 101, the imaging light source 103 and LED's 51 and 61; control of action of the LCD 39; control of movement of the focusing lens 31; control of movement of the reflection rod 67; control of movement of the focus optical system 60; control of action of the respective Galvano mirrors 43 and 44; and so on.

Further, as control of the OCT unit 100, the arithmetic and control unit 200 executes: control of action of the light source unit 101; control of movement of the reference mirror 114 and the collimator lens 113; control of action of the CCD image sensor 120; control of action of the attenuator 300; control of action of the light-blocking plate 400; and so on.

The arithmetic and control unit 200 includes a microprocessor, a RAM, a ROM, a hard disk drive, a communication interface, and so on, as in conventional computers. The storage device such as the hard disk drive stores a computer program for controlling the fundus observation apparatus 1. The arithmetic and control unit 200 may be provided with a circuit board dedicated for forming OCT images based on detection signals from the CCD image sensor 120. Moreover, the arithmetic and control unit 200 may be provided with operation devices (input devices) such as a keyboard and a mouse, and/or display devices such as LCD.

The retinal camera unit 2, display device 3, OCT unit 100, and arithmetic and control unit 200 may be integrally configured (that is, within a single case), or configured as separate bodies.

[Control System]

Figure 9:
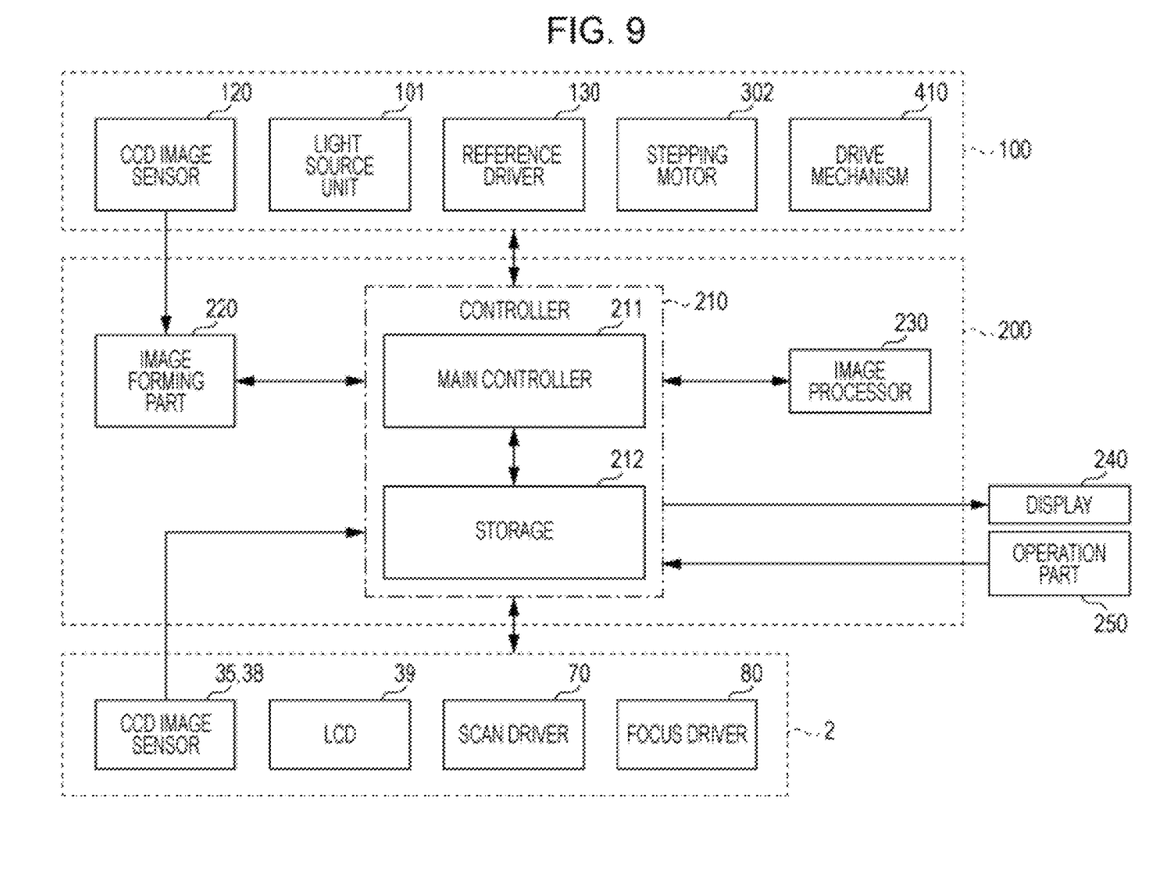
FIG. 9 is a schematic block diagram showing an example of a configuration of a control system of an embodiment of an optical image measurement apparatus (fundus observation apparatus) according to the present invention.

A configuration of a control system of the fundus observation apparatus 1 will be described with reference to FIG. 9.

(Controller)

The control system of the fundus observation apparatus 1 has a configuration centered on a controller 210 of the arithmetic and control unit 200. The controller 210 includes, for example, the aforementioned microprocessor, RAM, ROM, hard disk drive, and communication interface.

The controller 210 is provided with a main controller 211 and storage 212. The main controller 211 performs the aforementioned various kinds of control. Specifically, the main controller 211 controls a scan driver 70 as well as a focus driver 80 of the retinal camera unit 2, and further controls the light source unit 101, a reference driver 130, the stepping motor 302 and the drive mechanism 410 of the OCT unit 100.

The scan driver 70 is configured, for example, including a servo motor and independently changes the facing direction of the Galvano mirrors 43 and 44.

The focus driver 80 is configured, for example, including a stepping motor and moves the focusing lens 31 in the optical axis direction. Thereby, the focus position of light towards the fundus Ef is changed.

The reference driver 130 is configured, for example, including a stepping motor and integrally moves the collimator lens 113 as well as the reference mirror 114 along the travelling direction of the reference light LR.

The drive mechanism 410 moves the light-blocking plate 400 in the direction D. The drive mechanism 410 is configured to include a stepping motor and a mechanism that transfers a driving power of this stepping motor to move the light-blocking plate 400.

The main controller 211 executes a process of writing data into the storage 212, and a process of reading out the data from the storage 212.

The storage 212 stores various kinds of data. The data stored in the storage 212 is, for example, image data of OCT images, image data of fundus images, and eye information. The eye information includes information on the eye, for example, information on a subject such as a patient ID and a name, information on identification of left eye or right eye, and so on.

(Image Forming Part)

An image forming part 220 forms image data of a tomographic image of the fundus Ef based on the detection signals from the CCD image sensor 120. Like the conventional Fourier-Domain OCT, this process includes processes such as noise elimination (noise reduction), filtering, and FFT (Fast Fourier Transform).

The image forming part 220 includes, for example, the aforementioned circuit board and communication interface. It should be noted that "image data" and the "image" presented based on the image data may be identified with each other in this specification.

(Image Processor)

An image processor 230 executes various image processing and analysis on images formed by the image forming part 220. For example, the image processor 230 executes various correction processes such as luminance correction and dispersion correction of images.

Further, the image processor 230 executes, for example, an interpolation process of interpolating pixels between tomographic images formed by the image forming part 220, thereby forming image data of a three-dimensional image of the fundus Ef.

Image data of a three-dimensional image refers to image data that the positions of pixels are defined by the three-dimensional coordinates. The image data of a three-dimensional image is, for example, image data composed of three-dimensionally arranged voxels. This image data is referred to as volume data, voxel data, or the like. For displaying an image based on the volume data, the image processor 230 executes a rendering process (such as volume rendering and MIP (Maximum Intensity Projection)) on this volume data, and forms image data of a pseudo three-dimensional image taken from a specific view direction. On a display device such as the display 240, this pseudo three-dimensional image is displayed.

Further, it is also possible to form stack data of a plurality of tomographic images as the image data of a three-dimensional image. Stack data is image data obtained by three-dimensionally arranging a plurality of tomographic images obtained along a plurality of scanning lines, based on the positional relation of the scanning lines. That is to say, stack data is image data obtained by expressing a plurality of tomographic images defined by originally individual two-dimensional coordinate systems by a three-dimensional coordinate system (namely, embedding into a three-dimensional space).

The image processor 230 can form a tomographic image in any cross-section based on the image data of a three-dimensional image. This processing is executed, for example, by specifying, for the cross-section manually or automatically designated, a picture element (such as a voxel) located on this cross-section and arranging the specified image elements two-dimensionally to form image data that represents the morphology of the fundus Ef in the cross-section. Such processing enables images to be obtained not only in the cross-section of the original tomographic image (the position of the scanning line for the signal light LS) but also in any desired cross-section.

The image processor 230 includes, for example, the aforementioned microprocessor, RAM, ROM, hard disk drive, circuit board, and so on.

The image forming part 220 and the image processor 230 (in particular, its part forming three-dimensional images) are an example of an "image forming part" of the present invention.

(Display and Operation Part)

The display 240 is configured including a display device of the aforementioned arithmetic and control unit 200. The operation part 250 is configured including an operation device of the aforementioned arithmetic and control unit 200. Furthermore, the operation part 250 may also include various kinds of buttons or keys provided with the case of the fundus observation apparatus 1 or its outside. For example, if the retinal camera unit 2 has a case that is the same as conventional retinal cameras, a joy stick, operation panel, etc. provided with the case may also be included in the operation part 250. Furthermore, the display 240 may also include various display devices such as a touch panel monitor, etc. provided with the case of the retinal camera unit 2.

The display 240 and the operation part 250 do not need to be composed as separate devices. For example, like a touch panel LCD, a device in which the display function and the operation function are integrated can be used.

[Scan with Signal Light and OCT Image]

A scan with the signal light LS and an OCT image will be described.

The scan aspect of the signal light LS by the fundus observation apparatus 1 is, for example, a horizontal scan, vertical scan, cruciform scan, radial scan, circular scan, concentric scan, and helical scan. These scan aspects are selectively used as necessary in consideration of an observation site of the fundus, an analysis target (the retinal thickness or the like), a time required to scan, the accuracy of a scan, and so on.

A horizontal scan is a scan with the signal light LS in the horizontal direction (x-direction). The horizontal scan includes an aspect of scanning with the signal light LS along a plurality of scanning lines extending in the horizontal direction arranged in the vertical direction (y-direction). In this aspect, it is possible to set any interval between scanning lines. By setting the interval between adjacent scanning lines to be sufficiently narrow, it is possible to form the aforementioned three-dimensional image (three-dimensional scan). A vertical scan is also performed in a similar manner.

A cruciform scan is a scan with the signal light LS along a cross-shape trajectory formed by two linear trajectories (line trajectories) orthogonal to each other. A radial scan is a scan with the signal light LS along a radial trajectory formed by a plurality of line trajectories arranged at predetermined angles. The cruciform scan is an example of the radial scan.

A circular scan is a scan with the signal light LS along a circular trajectory. A concentric scan is a scan with the signal light LS along a plurality of circular trajectories arranged concentrically around a predetermined center position. The circular scan is an example of the concentric scan. A helical scan is a scan with the signal light LS along a helical trajectory while making the turning radius gradually smaller (or greater).

Because the Galvano mirrors 43 and 44 are configured to scan the signal light LS in the directions orthogonal to each other, they are capable of scanning with the signal light LS in the x-direction and the y-direction independently. Moreover, it is possible to scan with the signal light LS along an arbitrary trajectory on the xy-plane by simultaneously controlling the directions of the Galvano mirrors 43 and 44. Thus, it is possible to realize various types of scan aspects as described above.

By scanning the signal light LS in the mode described above, it is possible to form tomographic images of the depth-wise direction (z-direction) along scanning lines (scan trajectory). Moreover, in a case that the interval between scanning lines is narrow, it is possible to form the aforementioned three-dimensional image.

A region on the fundus Ef subjected to scanning by the signal light LS as above, that is a region on the fundus Ef subjected to OCT measurement, is referred to as a scanning region. A scanning region in three-dimensional scanning is a rectangular-shaped region in which multiple horizontal scans are arranged. Furthermore, a scanning region in a concentric circular scan is a disc-shaped region surrounded by the trajectories of a circular scan of a maximum diameter. Moreover, the scanning region in a radial scan is a disc-shaped (or polygonal-shaped) region linking end positions of scanning lines.

[Actions And Effects]

The actions and effects of the fundus observation apparatus 1 as described above will be described.

The fundus oculi observing device 1 is provided with an optical attenuator for adjusting the amount of interference light LC detected by the CCD image sensor 120. While the optical attenuator in this embodiment is provided in the reference optical path, the optical attenuator may be provided in an optical path of the low-coherence light L0, a signal optical path, and an optical path of the interference light LC. It is also possible to provide optical attenuators in any two of these optical paths, respectively. The optical path in which the optical attenuator is provided, that is, the optical path leading the light to be adjusted for the light amount, is sometimes referred to as the subject optical path.

The optical attenuator is configured to include the attenuator 300, the light-blocking plate 400, and the drive mechanism 410. The attenuator 300 and the drive mechanism 410 are each controlled by the arithmetic and control unit 200.

The attenuator 300 is configured to include the stepping motor 302, the cam 303, and the light-blocking link 310. The cam 303 has the cam face 303a shaped depending on the distribution of the light amount in the cross-section of the reference light LR. The cam 303 is rotated by the stepping motor 302. The light-blocking link 310 has the axis of rotation 311, the abutment 312, and the shield 313. The abutment 312 abuts on the cam face 303a. The axis of rotation 311 is provided at a predefined distance away from the abutment 312. The shield 313 is provided at a predefined distance away from the axis of rotation 311 and is capable of shielding the reference light LR from a first direction. These predefined distances are each set, taking into account various factors such as the amount of unit rotation of the stepping motor 302, the size of the cam 303 (the size of the cam face 303a), the size of the light-blocking link 310, the cross-sectional diameter of the reference light LR, and the resolution of shielding operation.

The light-blocking plate 400 is capable of shielding the reference light LR from a second direction different from the shielding direction (first direction) by the attenuator 300. The light-blocking plate 400 is moved by the drive mechanism 410 to change the shielding region.

When the cam 303 is rotated by the stepping motor 302, the abutment 312 moves following displacement of the cam face 303a with the rotation of the cam 303. The light-blocking link 310 rotates about the axis of rotation 311 with the movement of the abutment 312. The shield 313 moves in the first direction (direction D) with the rotation of the light-blocking link 310 to change the shielding region of the reference light LR.

In addition, it is possible to configure to operatively control the attenuator 300 and/or the light-blocking plate 400 in response to the operation with the operating part 250, and it is also possible to configure to operatively control the attenuator 300 and/or the light-blocking plate 400 automatically with reference to the received-light amount by the CCD image sensor 120.

The attenuator 300 and the light-blocking plate 400 are used as follows, for example. First, with both the attenuator 300 and the light-blocking plate 400 open, the interference light LC is received by the CCD image sensor 120. It is confirmed whether this received-light amount is appropriate or not. If the received-light amount is too much, the light-blocking plate 400 is moved to roughly adjust the received-light amount of the interference light LC.

Next, by changing the shielding region by the attenuator 300 while checking the received-light amount of the interference light LC, the received-light amount is precisely adjusted. Because the cam face 303a has a shape as described previously, precise adjustment is possible whether the shielding region of the reference light LR by the shield 313 is small or large.

After changing the shielding region of the reference light LR in this manner, that is, after the amount of the interference light LC received by the CCD image sensor 120 is adjusted, the fundus oculi observing device 1 detects interference light LC obtained by superposing the reference light LR, part of which is shielded by the attenuator 300 and the light-blocking plate 400, and the signal light LS. Furthermore, the fundus oculi observing device 1 forms an OCT of the fundus Ef based on the detection result of this interference light LC.

According to such a fundus oculi observing device 1, even for the case in which variation in the light amount of the interference light LC due to variation in the output light amount of the light source unit 101 and displacement of the collimator lens unit 107 occur, the light amount can be precisely adjusted using the attenuator 300 and the light-blocking plate 400. Thereby, the interference light LC can be suitably detected, and a good OCT image is obtained.

Moreover, for example, by devising the cam face 303a in the above-mentioned shape, it is possible to achieve the operational accuracy required in OCT measurement without using a stepping motor of particularly high resolution (i.e., small step angle). Particularly, even for the case in which the amount of light used is large, and interference light obtained by shielding majority of that light is detected, it is possible to adjust the light amount with high accuracy.

Furthermore, because it is configured to shield the reference light LR from two different directions, it is possible to precisely adjust the light amount. In addition, it is also possible to configure to shield the subject light from three or more different directions. This configuration is to shield the light from (at least) two directions, so it falls within the scope of the present invention.

In addition, the attenuator 300 and the light-blocking plate 400 do not require a complicated configuration. Therefore, the optical attenuator according to this embodiment can precisely adjust the light amount with a simple configuration.

MODIFIED EXAMPLE

The configuration described above is merely one example for favorably implementing the present invention. Therefore, it is possible to properly make arbitrary modification within the scope of the present invention.

It is possible to use a second shield that is different from the trapezoidal light-blocking plate 400 in the above-mentioned embodiment. For example, the second shield may be configured to pull and put a rectangular light-blocking plate that can be translated by the drive mechanism from and into the subject optical path. Moreover, the second shield may be configured to pull and put the rectangular light-blocking plate that is rotatable about the axis of rotation outside the subject light from and into the subject optical path.

Moreover, the second shield may be configured to shield only the region in the cross-section of the subject light where the light amount is large, that is, the central region of the cross-section. As such light-blocking plates, it is possible to use those provided with a light-blocking part in the central part of a transparent plate-like member. Moreover, a plate-like member comprised only of the light-blocking part may be hung with a thread-like member and arranged in the central region of the reference optical path. These light-blocking parts are formed into a disk shape, for example. The size of the light-blocking part in this variation may be configured to be changeable. By way of example, different sized light-blocking parts can be selectively used. It is also possible to continuously change the size of the light-blocking part using the structure that is similar to shutter blades comprised of multiple blades overlapped.

In the above-mentioned embodiment, the attenuator 300 with the first shield and the light-blocking plate 400 with the second shield are separately provided. In contrast, it is possible to allow the attenuator 300 to function as the second shield. By way of example, by configuring the attenuator 300 itself or the light-blocking link 310 to be moveable in the radial direction C in FIG. 3, the shielding operation in the radial direction C can be performed by the shield 313. The shielding operation in the rotational direction B is performed in the same manner as the above-mentioned embodiment. In addition, the attenuator 300 itself or the light-blocking link 310 is moved in the radial direction C by a drive mechanism not shown.

In the above embodiment, the position of the reference mirror 114 is changed so as to change an optical path length difference between the optical path of the signal light LS and the optical path of the reference light LR. However, a method for changing the optical path length difference is not limited thereto. For example, it is possible to change the optical path length difference by moving the retinal camera unit 2 and the OCT unit 100 with respect to the eye E to change the optical path length of the signal light LS. Moreover, in a case that an object is not a living site or the like, it is also effective to change the optical path length difference by moving the object in the depth direction (z-direction).

The computer program used in the above embodiments can be stored in any kind of recording medium that can be read by a computer. As this recording medium, for example, an optical disk, a magneto-optic disk (CD-ROM, DVD-RAM, DVD-ROM, MO, and so on), and a magnetic storage (a hard disk, a floppy Disk™, ZIP, and so on) can be used. Moreover, it is possible to store into a storing device such as a hard disk drive and a memory.

In addition, it is possible to transmit/receive this program through a network such as internet or LAN etc.

EXPLANATION OF SYMBOLS 1 fundus observation apparatus
2 retinal camera unit
3 display device
10 illumination optical system
11 observation light source
15 imaging light source
30 imaging optical system
31 focusing lens
35, 38 CCD image sensor
39 LCD
43, 44 Galvano mirror
50 alignment optical system
60 focus optical system
70 scan driver
80 focus driver
100 OCT unit
101 light source unit
114 reference mirror
118 diffraction grating
120 CCD image sensor
130 reference driver
200 arithmetic and control unit
210 controller
211 main controller
212 storage
220 image forming part
230 image processor
240 display
250 operation part
300 attenuator
302 stepping motor
303 cam
303a cam face
310 light-blocking link
311 axis of rotation
312 abutment
313 shield
400 light-blocking plate
410 drive mechanism
E eye
Ef fundus
G tomographic image

What is claimed is:

1. An optical image measurement apparatus comprising:
an optical system that splits light from a light source into signal light and reference light, generates and detects interference light by superposing the signal light that has passed through a signal optical path toward a measured object and the reference light that has passed through a reference optical path;
an image-forming part that forms an image of the measured object based on the detection result of the interference light; and
an optical attenuator that is respectively provided in at least one subject optical path of an optical path of the light from the light source, the signal optical path, the reference optical path, and an optical path of the interference light, and capable of shielding subject light traveling in the subject optical path;
the optical attenuator comprising:
a stepping motor;
a cam that has a cam surface shaped depending on the distribution of a light amount in the cross-section of the subject light, and that is rotated by the stepping motor;
a shielding mechanism including an abutment that abuts the cam face, an axis of rotation provided at a predefined distance away from the abutment, and a first shield that is provided at a predefined distance away from the axis of rotation and capable of shielding the subject light as the first shield is moved in a first direction; and
a second shield that is capable of shielding the subject light as the second shield is moved in a second direction, the second direction being different from the first direction, wherein, in response to the rotation of the cam by the stepping motor:
the abutment moves following the displacement of the cam face with the rotation of the cam;
the shielding mechanism rotates about the axis of rotation with the movement of the abutment;
the first shield moves in the first direction with the rotation of the shielding mechanism to change the shielding region of the subject light;
the optical system detects the interference light based on the subject light, part of which is shielded by the first shield and the second shield; and
the image-forming part forms an image of the measured object based on the detection result of this interference light, and
wherein the cam face is formed so that based on the distribution of the light amount, the first shield moves less in the first direction with each consecutive step of the stepping motor when increasing the shielding region than the first shield moves in the first direction with each consecutive step of the stepping motor when decreasing the shielding region.

2. The optical image measurement apparatus according to claim 1, wherein the distribution of the light amount is Gaussian.

3. The optical image measurement apparatus according to claim 1, wherein the optical attenuator comprises a drive mechanism that moves the second shield to change the shielding region of the subject light.

4. An optical image measurement apparatus comprising:
an optical system that splits light from a light source into signal light and reference light, generates and detects interference light by superposing the signal light that has passed through a signal optical path toward a measured object and the reference light that has passed through a reference optical path; and
an image-forming part that forms an image of the measured object based on the detection result of the interference light;
an optical attenuator that is respectively provided in at least one subject optical path of an optical path of the light from the light source, the signal optical path, the reference optical path, and an optical path of the interference light, and capable of shielding subject light traveling in the subject optical path;
the optical attenuator comprising:
a stepping motor;
a cam that has a cam surface shaped depending on the distribution of the light amount in the cross-section of the subject light, and that is rotated by the stepping motor;
a shielding mechanism including an abutment that abuts the cam face, an axis of rotation provided at a predefined distance away from the abutment, and a first shield that is provided at a predefined distance away from the axis of rotation and capable of shielding the subject light as the first shield is moved in a first direction; and a second shield that is capable of shielding the subject light as the second shield is moved in a second direction, the second direction being different from the first direction, wherein, in response to the rotation of the cam by the stepping motor:

the abutment moves following the displacement of the cam face with the rotation of the cam;

the shielding mechanism rotates about the axis of rotation with the movement of the abutment;

the first shield moves in the first direction with the rotation of the shielding mechanism to change the shielding region of the subject light;

the optical system detects the interference light based on the subject light, part of which is shielded by the first shield and the second shield; and the image-forming part forms an image of the measured object based on the detection result of this interference light, and wherein the optical attenuator comprises a drive mechanism that moves the second shield to change the shielding region of the subject light; a side of a tip of the first shield is formed in a substantially linear fashion in a radial direction relative to the rotational direction of the shielding mechanism about the axis of rotation;

a side of a tip of the second shield is formed in a substantially linear fashion, which is oblique relative to the radial direction so as to move the subject optical path up and down with the side of the first shield disposed at a position to shield the subject light; and the drive mechanism moves the second shield in a direction substantially perpendicular to the radial direction to change the shielding region of the subject light.

5. The optical image measurement apparatus according to claim 1, wherein the second shield shields only the central region of the cross-section of the subject light.

6. The optical image measurement apparatus according to claim 1, wherein the first shield and/or the second shield are disposed leaning to the cross-section of the subject light.

7. An optical attenuator that is capable of shielding a light beam, the optical attenuator comprising:

a stepping motor;

a cam that has a cam surface shaped depending on the distribution of the light amount in the cross-section of the subject light, and that is rotated by the stepping motor; and a shielding mechanism including an abutment that abuts the cam face, an axis of rotation provided at a predefined distance away from the abutment, and a first shield that is provided at a predefined distance away from the axis of rotation and capable of shielding the subject light as the first shield is moved in a first direction;

wherein, in response to the rotation of the cam by the stepping motor:

the abutment moves following the displacement of the cam face with the rotation of the cam;

the shielding mechanism rotates about the axis of rotation with the movement of the abutment; and the first shield moves in the first direction with the rotation of the shielding mechanism to change the shielding region of the light beam, wherein the cam face is formed so that based on the distribution of the light amount, the first shield moves less in the first direction with each consecutive step of the stepping motor when increasing the shielding region than the first shield moves in the first direction with each consecutive step of the stepping motor when decreasing the shielding region.

* * * * *